United States Patent [19]

Mitchell et al.

[11] 4,176,161
[45] Nov. 27, 1979

[54] OXIDATION OVER SYNTHETIC AMORPHOUS SILICAS

[75] Inventors: Thomas O. Mitchell, Trenton; Darrell D. Whitehurst, Titusville, both of N.J.

[73] Assignee: Mobil Oil Corporation, New York, N.Y.

[21] Appl. No.: 876,787

[22] Filed: Feb. 10, 1978

Related U.S. Application Data

[60] Continuation-in-part of Ser. No. 738,788, Nov. 4, 1976, abandoned, which is a continuation-in-part of Ser. No. 638,405, Dec. 8, 1975, Pat. No. 4,003,825, which is a division of Ser. No. 450,967, Mar. 14, 1974, Pat. No. 3,983,055.

[51] Int. Cl.$^2$ .............................................. B01D 53/34
[52] U.S. Cl. .................. 423/213.5; 423/245; 423/247
[58] Field of Search ................ 423/212, 213.2, 213.5, 423/245, 247, 336; 252/459, 460

[56] References Cited

U.S. PATENT DOCUMENTS

| | | | |
|---|---|---|---|
| 3,316,057 | 4/1967 | Stiles | 423/213.5 X |
| 3,397,034 | 8/1968 | Tulleners et al. | 423/213.5 |
| 3,619,127 | 11/1971 | Hass | 423/213.5 |
| 3,666,412 | 5/1972 | Sowards | 423/212 C X |
| 3,983,055 | 9/1976 | Mitchell et al. | 423/336 X |

FOREIGN PATENT DOCUMENTS

| | | | |
|---|---|---|---|
| 586487 | 4/1958 | Belgium | 423/213.5 |
| 436906 | 10/1935 | United Kingdom | 423/213.5 |

*Primary Examiner*—G. O. Peters
*Attorney, Agent, or Firm*—Charles A. Huggett; Raymond W. Barclay; Thomas S. Szatkowski

[57] ABSTRACT

Oxidation of suitable feedstock is provided wherein such feedstock is subjected to oxidation conditions in the presence of a catalytic amount of a solid containing, at least in part, a synthetic amorphous solid prepared by hydrolyzing and polymerizing in the presence of water a silane having the formula $R(Si)X_3$, wherein R is a non-hydrolyzable organic group, X is a hydrolyzable group and (Si) is selected from the group consisting of

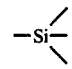

and

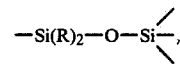

and calcining the polymerized product, said silane being admixed with a second compound, $R'_nMY_m$, wherein R' is selected from the group consisting of the same groups as R, Y is selected from the group consisting of the same groups as X and oxygen, M is at least one member selected from the group consisting of elements of Groups IIIA, IVA, IVB, VA, VB, VIB, VIIB and VIII of the Periodic Table, m is any number greater than 0 and up to 8 and n is from 0 to any number less than 8.

17 Claims, No Drawings

OXIDATION OVER SYNTHETIC AMORPHOUS SILICAS

CROSS-REFERENCE

This is a continuation-in-part of application Ser. No. 738,788, filed Nov. 4, 1976, now abandoned, which was a continuation-in-part of application Ser. No. 638,405, filed Dec. 8, 1975, now U.S. Pat. No. 4,003,825, which was a division of application Ser. No. 450,967, filed Mar. 14, 1974, now U.S. Pat. No. 3,983,055.

BACKGROUND OF THE INVENTION (1) Field of the Invention

This invention relates to use of specifically prepared amorphous synthetic siliceous materials as catalysts in oxidation of suitable chemical feedstock, such as, for example, hydrocarbons and/or carbon monoxide.

(2) Description of the Prior Art

U.S. Pat. No. 2,441,214 discloses a hydrocarbon conversion catalyst prepared by reacting an aluminum, magnesium or zirconium compound, such as $AlCl_3$, with dehydration product of a silanol or siloxane polymer $R_3SiOSiR_3$,

or

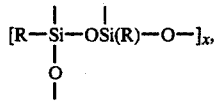

R being alkyl, aryl or aralkyl, to produce a metal complex, precipitating in water plus base ($NH_4OH$), water-washing and drying. In one example, the product was calcined for 3 hours at 500° C. This procedure is not the same as that utilized in the present invention, and it results in loss of silicon values with lower surface area and fewer small pores than desirable.

U.S. Pat. No. 2,483,963 discloses the hydrolysis of organochlorosilanes to produce organosiloxanes. The process involves introducing liquid silane into the upper end of a silane-water vapor contact zone and removing a condensed siloxane. The amount of water used is in excess of that necessary to hydrolyze the silane. The trichloro, $RSiCl_3$, in which R is alkyl or aryl, is either not used at all or used in a restricted amount so that in the formula $RnSiCl_{4-n}$, n is at least 1.7.

In U.S. Pat. No. 2,722,504 is disclosed a catalyst material having components of an activated silica or alumina, an oxide or sulfide of certain transition metals and an organophilic silicone coating formed by (1) adsorbing onto the activated surface of the first component a silane monomer of the formula

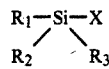

wherein X is a hydrolyzable group, $R_1$ is non-hydrolyzable and $R_2$ and $R_3$ may each be hydrolyzable or not (2) hydrolyzing the monomer, then (3) heating the combined materials at 800° F. to 1200° F. to dry; the second metal component is added by impregnation, or alternatively is added with the silane monomer.

In U.S. Pat. No. 3,661,770 there is disclosed a method of preparing a catalyst by using a chlorosilane compound, $SiX_4$, at least one of the X's being chlorine and the others hydrogen, methyl, ethyl, methoxy and ethoxy with a Group VIII metal-alumina composite at a temperature of 500° to 900° F. The composite is the catalyst and the silane is an activating agent.

SUMMARY OF THE INVENTION

It has now been discovered that shape-selectivity or the pore-size distribution of a silica or silica-containing composition may be controlled by the steps of (1) hydrolyzing a mono-organo silane, $R(Si)X_3$, alone or in the presence of other compounds having the formula $R'_nMY_m$, wherein the R groups and R' groups are organic non-hydrolyzable groups and may be the same or different, X is a hydrolyzable group, Y is the same as X or oxygen, and M is either a metal or non-metal of the groups of the Periodic Table including silicon other than Groups IA, IIA, VIIA and O, m is a number up to 8 and n is zero or a number less than 8, or an inorganic ionic compound containing M and Y, (2) bringing about the condensation and polymerization of the hydrolyzed compounds and (3) calcining the polymerized product. It has further been discovered that the calcined silica-containing products above have utility in a process for oxidation of suitable organic compound feedstocks, such as, for example, hydrocarbons, especially low molecular weight hydrocarbons, and carbon monoxide. Said hydrocarbons and carbon monoxide may be components of the exhaust effluent from internal combustion engines.

In the following discussion, "silica products" or "silica structures" and similar terms are intended to include materials as described herein, containing components other than silica alone. Also as used herein, the term "hydrolyzable" refers to any group which is capable of conversion to hydroxy in the presence of water under conditions of the hydrolysis step; "non-hydrolyzable" refers to any group which does not convert to hydroxy under the said conditions.

DESCRIPTION OF SPECIFIC EMBODIMENTS

This invention provides an oxidation process utilizing as a catalyst a solid having shape-selectivity for hydrocarbon conversion and other processes but without the cost of many of the known shape-selective catalysts. The present invention provides inexpensive catalysts of controlled pore size whose adsorptive characteristics can be designed to accept within the pores thereof hydrocarbon molecules of different shapes. Furthermore, this invention provides a silica structure which may be used alone as a catalyst or as the selective carrier for more active components.

Formation of the silica structures for use in this invention is carried out by the steps of hydrolyzing the silane, polymerizing the hydrolysis products and calcining the polymerized product. The silanes used in formation of the silica structures useful in this invention have the formula $R(Si)X_3$ wherein R is an organic radical which cannot be hydrolyzed in the above hydrolyzing step and X is a hydrolyzable group which ultimately converts the silane to a siloxane polymer. As used in this invention, R may be alkyl, cycloalkyl, alkenyl, cycloalkenyl, aryl, alkaryl, aralkyl, or a heterocylic group containing oxygen, sulfur or nitrogen in the ring, aminoalkyl (including polyamino alkyl), and the halo and hydroxy derivatives of such geoups, R having preferably from 1 to about 40 carbon atoms; the expression (Si) may be a single silicon atom or

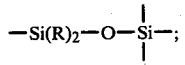

X may be halogen, hydrogen, alkoxy, aryloxy or from 1 to about 20 carbon atoms, alkali metaloxy, carboxy, nitro, amino and the like. The preferred compounds for use in forming the silica structure useful in this invention are those in which R is alkyl or aryl or a group containing one or more amino groups and X is halogen or alkoxy. Non-limiting examples of R include methyl, ethyl, butyl, hexyl, decyl, dodecyl, octadecyl, phenyl, tolyl, naphthyl, aminomethyl, aminoethyl, aminopropyl, ethylenediaminomethyl, ethylenediaminopropyl, cyclohexyl, chlorobutyl, hydroxybutyl, ethoxyethyl, propoxypropyl and the like. Non-limiting examples of X include chloro, bromo, iodo, methoxy, ethoxy, acetoxy and the like.

Normally hydrolysis would convert hydrolyzable groups to hydroxy. However, trihydroxy organosilanes would lead instead to organosiloxane polymers by dehydrocondensation molecular weights ranging from 2500 to 3,000,000 or more are usually obtained.

Depending on the amount of water present in the hydrolysis reaction mixture and the type of R group, the intermediate polymerization product is either a three-dimensional cage-containing structure or a two-dimensional linear or sheet-containing structure. The cage-containing structure is the preferred structure in this invention for producing the more desirable silica, although it is likely that the hydrolysis step produces both types of polymer in the same reaction mixture. For this reason, the amount of water used in the hydrolysis is preferably kept to the stoichiometric amount or slightly in excess of that necessary to convert the X groups to hydroxy. It is preferred to use a system of an organic solvent and water instead of water alone. Excess water also has been found to affect the distribution of the pore sizes in the finished calcined product. It is preferred to use 0.5:1 to 10:1 by volume of organic solvent to water. The preferred solvents are hydrocarbons, e.g. hexane and benzene, ethers and alcohols, the preferred alcohols being methanol, ethanol and other lower alcohols. However, solubility of the silane in the water-solvent system is not necessary, providing the water control is maintained throughout the hydrolysis step. Hence, any convenient solvent system is useful.

The silane is added to the solvent-water mixture and stirred. An acid or base hydrolysis/condensation catalyst may be used. Hydrolysis may be effected at a temperature as low as room temperature and up to about 200° C. Usually, a solid precipitate or a thick syrup is produced. The precipitated polymer may be separated from the reaction mixture by filtration. The semi-solid polymer may be separated by boiling off the liquids preferably under vacuum. The remaining structure is understood to consist of the following repeating group:

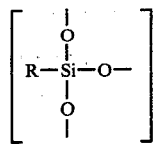

If the silane is hydrolyzed alone, without a second dissimilar component present, the polymeric structure is understood to be primarily a cage-type three-dimensional network molecule. Other silanes may be present in the hydrolysis step. Other tri-X silanes of different R groups or mono-X or di-X silanes of the same or different R groups will provide a cage molecule of differing channels or pore characteristics. Generally, the R group determines the size of the pores of the final product, the smaller the R group the smaller the pore.

The siloxane polymer resulting from the hydrolysis step is then subjected to stepwise or programmed calcining. Essentially, calcining replaces the R groups of the polymer with hydroxy, or oxy groups depending upon whether pairs of hydroxy groups are formed close enough to each other to condense or, if calcining is done in the absence of air, hydrogen. Clearly the gaps caused by the removed R groups form the small pores. Calcining is carried out at the minimum elevated temperatures necessary to remove the R groups, normally from about 200° C. to below the sintering temperature, usually 200° C. to 600° C., preferably from 350° C. to 550° C., and at rates of increase from 10° C. to 300° C. per hour, preferably 20° C. to 250° C. (or from 0.3° C. to about 4° C. per minute).

When the calcining step is carried out in air, hydroxy or oxy or even —M—O— groups (if a second component is present) occur in the product. In the absence of air, it is believed that

groups occur by free radical mechanism.

Preparation of a small pore size material with a high degree of cross-linking (three-dimensional structure) may be obtained by using $R(Si)X_3$ alone or with other silanes in which R is a low alkyl. Some selectivity for particular hydrocarbon molecules to be sorbed, otherwise obtainable with $R(Si)X_3$, may be lost in final products obtained when $SiX_4$, $R_2(Si)X_2$ or $R_3(Si)X$ are in the initial reaction mixture. Since control of shape selectivity is one of the desirable ends of this invention, as well as producing stable three-dimensional structures, it is more preferred that the $R(Si)X_3$ be the only silicon reactant; if a mixture of silanes is used, it is preferred that at least about 33% by weight of the silanes be $R(Si)X_3$. For example, a product derived from phenyl trichlorosilane has a slightly lower pore volume than that of a product obtained from a mixture of 80% phenyl trichlorosilane and 20% diphenyl dichlorosilane, but the selectivity for n-hexane was higher in the first product.

Surface areas also vary with R, methyl producing a relatively low area, bulkier groups such as cyclohexyl or phenyl producing products of over 300 m²/g.

The R(Si)X$_3$ silane may be hydrolyzed in the presence of R'$_n$MY$_m$, in which R' is the same as or different from R, Y is any combining group, preferably halogen or alkoxy, aryloxy, metaloxy, hydroxy or oxy, M is a metal or non-metal, preferably of Periodic Groups IIIA, IVA, IVB, VA, VB, VIB, VIIB and VIII, m is a number up to 8, and n is 0 or a number less than 8. In addition, inorganic ionic compounds consisting of an anion of M and Y with a cationic portion may be used. Suitable cations include hydrogen, alkali and alkaline earth metals and ammonium. An M-containing compound may also be a complex having as one ligand a suitable group such as amine or phosphine which latter is part of an R group on silicon. In particular, the amorphous silica solids of this invention may have incorporated therewith molybdenum, boron, tin, silver, tungsten, chromium, copper, iron, manganese, zinc, zirconium, titanium, phosphorus, vanadium, cobalt, nickel, palladium, platinum, and the like, and mixtures thereof with each other and/or with aluminum.

The second component is combined with the R(Si)X$_3$ in a solvent system in the hydrolysis step. These combination products, as with the silica products alone, are also amorphous solids of varying pore sizes and surface areas.

The silane is combined with one or more members of the second component in the presence of water and solvent, again water being in preferably stoichiometric, or only slightly over stoichiometric amounts. If necessary a small quantity of a base acting as a catalyst for promoting the polymerization of the mixture may be present, such as pyridine, pyrimidine, triethylamine or ammonia. The resulting solid is removed and subjected to calcination to produce the desired material.

Such compounds as aluminum chloride, aluminum butoxide, aluminum ethoxide, aluminum propoxide, sodium aluminate, ethyl aluminum chloride, methyl aluminum chloride, boric acid, sodium borate, methyl borate, cobalt chloride, nickel chloride, nickel acetate, phenyl phosphite or phosphonate, butyl phosphonate, phenyl dichlorophosphine, palladium chloride, methylamine palladium chloride, palladium nitrate, chloroplatinic acid, potassium chloroplatinate, cyclooctadienyl platinum dichloride, butyl tin acetate, tin chloride, dicyclopentadienyl titanium chloride, titanium chloride, vanadium chloride, vanadium oxide are suitable as the second component in this invention. Second components containing Group VIII metals, such as, for example platinum and/or palladium, are preferred.

In addition, known methods of exchange or impregnation can be used to incorporate additional metals for the purpose of producing catalysts.

In general, hydrocarbon compounds and carbon monoxide may be completely catalytically oxidized to carbon dioxide (in the case of carbon monoxide) or carbon dioxide and water (in the case of hydrocarbons) in the presence of a catalytic amount of the above-defined specifically prepared siliceous material over a range of catalytic conditions, including a temperature of from about 50° C. to about 1000° C., a pressure of from about 0.1 atmosphere to about 10 atmospheres and a gas hourly space velocity (GHSV), espressed at standard temperature and pressure, of from about 1,000 hr$^{-1}$ to about 70,000 hr$^{-1}$. An excess of oxygen of at least about 50 percent of that stoichiometrically required is provided for the present process where complete oxidation is desired. In fact, the excess of oxygen may be as much as 1000 percent or more of that stoichiometrically required. Partial oxidation of certain hydrocarbon compounds may be realized by the present process by judiciously limiting catalytic activity of the catalyst, utilizing a temperature low in the above range and/or avoiding the presence of oxygen in excess of stoichiometric requirements.

Oxidation products of carbon dioxide and water result from the complete oxidation under the above conditions of hydrocarbon compounds, such as olefins of from 2 to about 35 carbon atoms, paraffins of from 1 to about 35 carbon atoms, aromatics of from 6 to about 35 carbon atoms and alkyl-substituted aromatics of from about 7 to about 35 carbon atoms, including, as non-limiting examples, methane, ethane, butane, pentane, hexane, octane, ethylene, butylene, pentene, methylbutane, dimethylbutane, cyclohexane, benzene, toluene, naphthalene and others. Products of partial oxidation of hydrocarbon compounds under the above conditions include, as non-limiting examples, anhydrides, alcohols, aldehydes, ketones, acids and phenols. For example, partial oxidation of toluene by way of the present process leads to a product of benzaldehyde. Partial oxidation of benzene provides maleic anhydride; of naphthalene, phthalic anhydride; of propylene, acrolein ($CH_2=CHCHO$); and of ethylene, acetaldehyde.

In particular, when the oxidation process is conducted in an industrial setting, such as, for example, a refinery or chemical plant, the reaction conditions should be maintained within certain critical ranges, including a temperature of from about 150° C. to about 1000° C., preferably from about 150° C. to about 400° C., a pressure of from about 0.1 atmosphere to about 10 atmospheres, preferably from about 0.5 atmosphere to about 2 atmospheres, and a GHSV, expressed at standard temperature and pressure, of from about 5,000 hr$^{-1}$ to about 40,000 hr$^{-1}$.

When the oxidation process is conducted with a feedstock comprising the exhaust effluent from an internal combustion engine, such as for example, exhaust from an automobile, the reaction conditions should be maintained within certain other critical ranges, including a temperature of from about 150° C. to about 900° C., preferably from about 700° C. to about 800° C., a pressure of about atmospheric, and a GHSV, expressed at standard temperature and pressure, of from about 15,000 hr$^{-1}$ to about 70,000 hr$^{-1}$.

The following examples represent illustrations of the present invention and are not meant to be limitations thereof. Unless otherwise expressed, amounts and percentages are on a weight basis. Percent yields of the final calcined products are based on the weight of the polymer produced after hydrolysis and polymerization.

EXAMPLE 1

In a suitable vessel was added 25 ml of phenyl trichlorosilane to a solution of 15 ml of water and 60 ml of methanol (1:4 v/v). The heat generated by this addition brought the mixture to boiling and white solid formed. The mixture was maintained at room temperature for four days, after which the solid was removed and washed in ethanol and air dried. The washed solid was calcined in air by heating at 100° C. per hour to 500° C. and held at that temperature for 10 hours.

The resulting product was amorphous by X-ray examination and had the following characteristics:

| | |
|---|---|
| Surface Area: | 511 m$^2$/gm |

-continued

| | |
|---|---|
| Means Pore Diameter: | 26 A |
| Pore Volume: | 0.341 ml/gm |
| Particle Density: | 1.28 g/ml |
| Real Density: | 2.32 g/ml |

| Pore Size Distribution | |
|---|---|
| less than 7 A | 61.0% |
| 7–10 | 8.0 |
| 10–15 | 3.4 |
| 15–25 | 1.4 |
| 25–300 | 2.1 |
| over 300 | 24.1 |

EXAMPLE 2

In a suitable reactor, 50.4 grams of $H_2NCH_2CH_2NHCH_2CH_2CH_2Si(OCH_3)_3$ was added to 150 ml of the 4/1 v/v methanol-water mixture of Example 1. The mixture was stirred for one hour and allowed to stand for one day. The mixture was then refluxed for 2 hours and the solvent removed under vacuum. The resulting product was calcined at 3° C. per minute to 538° C. and held for 10 hours and then cooled. The yield was 35% by weight based on the weight of polymer. The product had a surface area of 642 m²/gram.

EXAMPLE 3

In a suitable reactor, 50 grams of $BrCH_2CH(Br)—SiCl_3$ was added to 150 ml of the 4:1 v/v methanol-water solvent. The mixture was allowed to stand for 2 days. It was refluxed for 2 hours and filtered. The solids were washed with three 200-ml portions of ethanol and dried in a vacuum oven at 125° C. for 2 hours. The product was calcined by heating at 1° C. per minute to 538° C., and held at that temperature for 10 hours, and finally cooled. The yield was 27% by weight and the product had a pore volume of 0.15 ml/g, surface area of 242 m²/g and a particle density of 1.66 g/ml.

EXAMPLE 4

In a suitable reactor, 50.5 grams of dodecyltrichlorosilane $C_{12}H_{25}SiCl_3$ was added to 150 ml of the methanol-water 4/1 v/v solvent and the mixture was allowed to stand for 4 days. The mixture was then refluxed at about 60° C. for 2 hours. The product polymer was a viscous liquid. The solvent was decanted and polymer washed three times with 200-ml ethanol portions with decanting of the wash each time. The washed product was dried in a vacuum oven at 120° C. for 2 hours, calcined at 1° C. per minute to 538° C., held at that temperature for 10 hours and cooled. The yield was 20% by weight of a product having the following characteristics: pore volume 0.233 ml/g, surface area 178 m²/g and particle density 1.59 g/ml.

EXAMPLE 5

A mixture of 55 grams of triphenylhydroxy silane, $(C_6H_5)_3SiOH$, 8 grams of sodium and 300 ml of benzene was refluxed at 80° C. for 3 hours and allowed to stand without heat for 5 days. The mixture was cooled to about 10° C. in an ice bath and stirred, and 40 grams of $SiCl_4$ in 200 ml benzene was added. The resulting mixture was subjected to reflux at 80° C. for 2 hours and cooled. During the $SiCl_4$ addition and refluxing, a stream of helium was passed through the reactor to exclude moisture. The reaction mixture was filtered to remove solid by-product. The benzene was then removed on a rotary evaporator to leave 39.7 grams of the product $(C_6H_5)_3—Si—O—SiCl_3$.

In a suitable reactor, 29.6 grams of the above product was added to 150 ml of the same methanol-water solvent and the mixture was allowed to stand one day. The mixture was then refluxed at 60° C. for 2 hours and cooled and allowed to stand for 7 days. The viscous white liquid was separated from the supernatant solvent, washed three times with 200-ml portions of ethanol. After the first wash, the product was a granular solid. The washed product was dried in a vacuum oven at 120° C. for 2 hours and calcined at 1° C. per minute to 538° C., being held at that temperature for 10 hours. The yield was 23% by weight; pore volume 0.21 ml/g, surface area 341 m²/g, particle density 1.59 g/ml.

EXAMPLE 6

In a suitable reactor, 25 grams of phenyl trichlorosilane and 25 grams of methyl trichlorosilane were added to 150 ml of the 4/1 methanol-water solvent. The mixture was allowed to stand for 2 hours and then refluxed for 2 hours. The solvent was decanted and the white solid washed three times with 100-ml portions of water, three times with 100-ml portions of acetone and three times with 100-ml portions of hexane. The product was dried in a vacuum oven at 118° C. for 1.5 hours then calcined as in Example 5. The yield was 62% by weight; surface area 355 m²/g.

EXAMPLE 7

A silica compound prepared as in Example 2 was produced by adding to 150 ml of a 4/1 v/v mixture of methanol and water 10 grams of $SiCl_4$, 4 grams of methyl trichlorosilane, 33.5 grams of dimethyl dichlorosilane and 2 grams of trimethyl chlorosilane. The calcination yielded 66% by weight of final product. This product had a pore volume of 0.79 ml/g, a surface area of 94 m²/g and a particle density of 0.8 g/ml.

EXAMPLE 8

In a suitable reactor 42 grams of phenyl trichlorosilane and 10.3 grams of diphenyl dichlorosilane were added to 150 ml of the 4/1 by volume methanol-water solvent. The mixture was allowed to stand for 6 days. The solvent was decanted and the product was washed three times with 300-ml portions of ethanol. The product was dried in a vacuum oven for 16 hours and calcined as in Example 5. The yield was 27% by weight.

EXAMPLE 9

In a suitable reactor, 100 ml of ethyl trichlorosilane was added to 300 ml of the same methanol-water solvent mixture of the previous examples. The mixture was allowed to stand for 10 days, then heated to reflux for one-half hour and again allowed to stand for 2 days. The solvent was boiled off over a 2-hour period and the product was washed three times with 100-ml portions of ethanol and three times with 100-ml portions of petroleum ether. The product was air-dried, calcined at 9° C. per minute to 538° C. held at that temperature for 10 hours and then cooled. The yield was 73% by weight; pore volume 0.22 ml/g, surface area 90 m²/g and particle density 1.44 g/ml.

EXAMPLE 10

In a suitable reactor 50 grams of methyl trichlorosilane was mixed with 150 ml of the 4/1 v/v methanol-water solvent. The mixture was allowed to stand for 7 days. The solvent was decanted and the product washed three times with 100-ml portions of ethanol. The product was dried in a vacuum oven at 120° C. for one hour and calcined as in Example 5. The yield was 85%, pore volume 0.16 ml/g, surface area 28 $m^2$/g and particle density 1.62 g/ml.

A number of silica products were tested for sorption capacity in the following manner. A sample solid of known weight is placed in a quartz basket suspended from a microbalance (Cahn Instrument Co.) on a quartz rod, all enclosed in a jacketed heater. A carrier gas, helium, is passed through a wick saturator to entrain water or hydrocarbon vapor and then into the microbalance and basket at 100 ml/min. Temperature and weight measurements of the solid are continuously made. The temperature is maintained at 35° C. in the heater. The sorption capacities are reported at partial pressures in the carrier stream of 20 mm. Hg for hydrocarbons, 12 mm. for water. The following are results for sorption of n-hexane, 2,3-dimethylbutane, water, cyclohexane, benzene and triethylamine. For comparison purposes, an aluminosilicate zeolite catalyst of the ZSM-5 type, described in U.S. Pat. No. 3,702,886, in which the cations are predominantly hydrogen (herein referred to as "HZSM-5"), was also measured by sorption capacity.

| Example | $nC_6$ | 2,3-DMB | $H_2O$ | $CycC_6$ | $C_6H_6$ | TEA |
| --- | --- | --- | --- | --- | --- | --- |
| 1 | 0.17 | 0.13 | 0.15 | 0.13 | 0.17 | 0.05 |
| 2 | 0.32 | 0.27 | 0.27 | — | — | — |
| 3 | 0.13 | 0.06 | 0.10 | — | — | — |
| 4 | 0.09 | 0.02 | 0.10 | 0.04 | 0.09 | — |
| 8 | 0.10 | 0.11 | 0.16 | — | — | — |
| 9 | 0.09 | 0.01 | 0.12 | 0.06 | 0.07 | — |
| 10 | 0.008 | 0.006 | 0.005 | — | — | — |
| HZSM-5 | 0.19 | 0.16 | 0.09 | — | — | 0.12 |

EXAMPLE 11

To a solution of 50 grams of phenyl trimethoxysilane, $C_6H_5Si(OCH_3)_3$, and 10 ml of pyridine in 150 ml of 4:1 methanol-water v/v mixture were added 5 grams of aluminum t-butoxide, $Al(O-t-C_4H_9)_3$. The mixture was allowed to stand overnight and was then heated to reflux at about 60° C. for 6 hours. Upon cooling the mixture, a solid precipitated. The solid was filtered out, washed with ethanol, dried in a vacuum oven and heated to 538° C. at 1° C./minute in an air stream. It was then cooled yielding 11.3 grams of a brown-gray aluminum-silicon solid.

EXAMPLE 12

In a suitable reactor 31.3 grams of ethyl trichlorosilane, $CH_3CH_2SiCl_3$, 150 ml of the 4:1 methanol-water mixture and 3 grams of 1,5-cyclooctadienyl platinum dichloride were combined. Heat evolved and the mixture became opaque. After standing overnight, the light yellow solid and clear liquid so resulting were refluxed at about 60° C. for 16 hours and cooled. The solid was filtered out, washed and dried and calcined as in Example 11, leaving 8.8 grams of a black granular platinum-silicon product.

EXAMPLE 13

To a vessel containing 750 ml of water was added 82.9 grams of methyl trichlorosilane, the temperature rising to 56° C. The mixture was stirred for 10 minutes and a white solid precipitate was filtered out, water washed and added to a solution of 20.2 grams of NaOH (equimolar to silicon) in 63 grams of water. The resulting mixture was stirred for 2 hours at 100° C., then 168 grams of methanol was added. Minor solid matter was removed by filtration, leaving as filtrate an aqueous solution of $CH_3Si(OH)_2ONa$. To this solution were added 24 grams of nickel chloride hexahydrate and 13.3 grams of aluminum chloride (equimolar amounts) dissolved in 150 ml of the 4:1 alcohol:water mixture. A light green solid precipitated; an additional 150 ml of solvent mixture was added and the system was heated to reflux at about 70° C. for 2 hours. The solid product was separated from the supernatant liquid after standing for 16 hours at room temperature. Sodium chloride was removed with boiling water and methanol, and the washed solid was dried in vacuum at 120° C. The product was calcined as in Example 11, providing a yield of 38.6 grams of a light tan nickel-aluminum-silicon solid.

EXAMPLE 14

To a vessel containing 200 ml of absolute ethanol were added 0.839 grams of $PdCl_2$ and 51.6 grams of aminoethylaminopropyl tirmethoxysilane (the $H_2NCH_2CH_2NHCH_2CH_2CH_2Si(OCH_3)_3$ of Example 2). After standing overnight the mixture was filtered to remove solid $PdCl_2$ particles and 50 ml of water was added producing a light yellow solution. No precipitate formed after 5 days of standing; the solvent was removed under vacuum, below 33° C., leaving a light yellow solid. The solid was calcined as in the previous examples; 14.3 grams of a red-brown palladium-silicon solid was produced containing about 3% palladium.

EXAMPLE 15

In a suitable reactor, 10 grams of aluminum tri-isopropoxide and 50.6 grams of $H_2NCH_2CH_2NHCH_2CH_2CH_2Si(OCH_3)_3$ were added to 150 ml of the 4/1 methanol-water solvent and allowed to stand one day. The mixture was refluxed at 60° C. for 2 hours and allowed to stand one more day. It was again refluxed for 96 hours. A liter of methanol was added and the mixture was heated to boiling, then filtered while hot. The solvent was removed from the filtrate with a rotary evaporator, dried in a vacuum oven at 120° C. for 4 hours, then calcined as in Example 11. The yield was 51.2%.

EXAMPLE 16

In a suitable reactor 50.9 grams of $H_2NCH_2CH_2NHCH_2CH_2CH_2Si(OCH_3)_3$, 3.35 grams of aluminum triethoxide and 10 ml of pyridine were mixed with 50 ml $H_2O$ and 200 ml of methanol and the mxiture was heated to reflux for 16 hours. The solvent was stripped under vacuum and the product was calcined at 3° C. per minute to 538° C., held at that temperature for 10 hours and cooled. The yield was approximately 47%.

EXAMPLE 17

In a suitable reactor, 50 grams of phenyl trichlorosilane and 15 grams of boric acid were added to 150 ml of tetrahydrofuran. The mixture was stirred for 2 hours, refluxed for 2 hours and allowed to stand for 48 hours. The solvent was stripped off with the rotary evaporator under house vacuum at 100° C. The product was calcined as in Example 16, but at a rate of 2° C. per minute. The yield was 34%.

EXAMPLE 18

In a suitable reactor, 10 ml of phenyl trimethoxysilane, $C_6H_5Si(OCH_3)_3$, 5 grams of vanadium oxy acetylacetonate, 200 ml methanol, 25 ml of water and 5 ml of triethylamine were mixed together and allowed to stand for 10 days. The resulting product was filtered out and washed three times with 100-ml portions of methanol, dried in a vacuum oven at 120° C. for 2 hours. The washed product was calcined at 1° C. per minute to 538° C., held at that temperature for 10 hours. The yield of vanadium-silicon product was about 50.4% by weight.

EXAMPLE 19

In a suitable reactor, 10 ml of methyl trichlorosilane, 5 ml of dibutyl tin diacetate, 200 ml of methanol and 25 ml of water were mixed and allowed to stand for 10 days. The product was treated as in Example 18. The yield of tin-silicon product was about 67% by weight.

EXAMPLE 20

In a suitable reactor were mixed 33 grams of phenyl trichlorosilane and 40 grams of phenyl phosphonic acid in 30 ml of methanol and the mixture was refluxed for 16 hours. The solvent was removed under vacuum on a rotary evaporator. The product was an amber viscous material; it was dissolved in 100 ml of boiling acetone. The acetone was removed by evaporation leaving solid product. Calcining at 3° C. per minute to 538° C., holding for 10 hours at that temperature left a 33.8% yield of phosphorus-silicon product.

EXAMPLE 21

In a suitable reactor were mixed 94.1 grams of phenyl trichlorosilane, 3.34 ml of a solution of 0.113 gram/ml of sodium ethyl chloroplatinate in ethanol and 15.8 grams of phenyl dichlorophosphine. Slowly added dropwise to the mixture was 200 ml of a 1/1 by volume methanol-water mixture. Foaming and a heavy white precipitate resulted. The product was filtered out, washed with about 2000 ml of methanol and calcined as in Example 18. A 25% yield of phosphorus-platinum-silicon product was obtained.

EXAMPLE 22

A solution of $CH_3Si(OH)_2ONa$, prepared as in Example 13, was mixed with 24.1 grams of $CoCl_2.6H_2O$ and 13.3 grams of aluminum chloride dissolved in 150 ml of the 4/1 v/v methanol-water solvent. Another 150-ml solvent portion was added, the mixture was refluxed for 2 hours and then cooled. Solids were filtered out, and 1000 ml of boiling water was passed through the filter paper to remove NaCl. The solids were washed three times with 500-ml portions of methanol, dried in a vacuum ovean at 120° C. for 16 hours and calcined at 3° C. per minute to 500° C., being held at that temperature for 10 hours, and finally cooled. The yield of cobalt-aluminum-silicon product was 84.4%.

The physical characteristics of the products of Examples 11 to 22 are as follows:

| Product of Example | Percent of M | Pore Volume, ml/g | Surface Area, m$^2$/g | Particle Demsity, g/ml |
|---|---|---|---|---|
| 11 | 6.3 (Al) | 0.284 | 334 | 1.52 |
| 12 | 3.19(Pt) | 0.086 | 117 | 1.94 |
| 13 | 13.2 (Ni) | | | |
| 14 | 6.8 (Al) | 1.43 | 240 | 0.56 |
|    | 3.0 (Pd) | 0.512 | 832 | 1.06 |
| 15 | 9.7 (Al) | — | 52 | — |
| 16 | 1.1 (Al) | — | 296 | — |
| 17 | 7.72(B) | — | below 5 | — |
| 18 | 0.22(V) | — | — | — |
| 19 | 0.1 to 1.0 (Sn) | — | — | — |
| 20 | 24.0 (P) | 1.345 | 35 | 0.542 |
| 21 | 0.5 (P) 0.02(Pt) | — | 354 | — |
| 22 | 15.2 (Co) | 1.030 | 191 | 0.740 |

EXAMPLE 23

The product catalyst of Example 12 was tested in a hydrocarbon-CO feed oxidation test which indicates oxidation activity for catalytic converters in automobiles. The product catalyst contained 3.19% platinum.

The test was conducted by passing a synthetic auto exhaust gas (2.04% by volume of carbon monoxide, 427 ppm of propylene, 4.79% by volume of oxygen, 10.2% by volume of carbon dioxide and the balance nitrogen) over a 5 mg catalyst sample at a GHSV, expressed at standard temperature and pressure, of 17,000 and atmospheric pressure. The temperature was raised 10° C. per minute and the effluent gas was analyzed. For comparison purposes, a standard commercial catalyst, 7.5% platinum on gamma-alumina (by impregnating with tetraamine platinum chloride) was also tested. The results show the temperatures for the indicated percent conversion of carbon monoxide and propylene.

| Percent Conv. (CO + $C_3H_6$) | Temperature, °C. | |
|---|---|---|
| | Standard | Example 12 |
| 0 | 150 | 107 |
| 10 | 165 | 135 |
| 25 | 173 | 150 |
| 50 | 178 | 158 |
| 90 | 178 | 165 |
| 100 | 178 | 170 |

As evidenced by the above results, the product of Example 12 has superior oxidation activity over the standard commercial catalyst.

As indicated previously, the silica structures of this invention may be controlled to have shape selectivity toward certain hydrocarbon molecules. One desirable small pore size distribution will accept normal molecules and exclude branched isomers. The incorporated components with the silica do not effect this shape selectivity adversely. Pore size distributions (in percent) are as follows:

| Pore Radius, A | Ex. 11 | Ex. 12 | EX. 14 |
|---|---|---|---|
| below 7 | 35.7% | 24.6 | 0.0 |
| 7–10 | 8.4 | 18.9 | 50.8 |
| 10–15 | 1.6 | 26.4 | 27.2 |
| 15–25 | 0.3 | 2.4 | 2.3 |
| 25–50 | 0.0 | 3.3 | 0.3 |
| 50–75 | 0.0 | 2.9 | 0.4 |

-continued

| Pore Radius, A | Ex. 11 | Ex. 12 | EX. 14 |
|---|---|---|---|
| 75–100 | 0.0 | 2.4 | 0.2 |
| 100–200 | 0.0 | 4.0 | 0.3 |
| 200–300 | 0.0 | 1.1 | 0.2 |
| over 300 | 54.0 | 14.0 | 18.3 |
| Total Vol. | 0.284 | 0.086 | 0.512 |
| Vol. Below 15 A | 0.130 | 0.060 | 0.399 |

What is claimed is:

1. An oxidation process comprising contacting an exhaust effluent from an internal combustion engine with a solid catalytic material in the presence of oxygen and under conditions including a temperature from about 150° C. to about 900° C., a pressure of about atmospheric and a gas hourly space velocity, expressed at standard temperature and pressure, of from about 15000 hr$^{-1}$ to about 70,000 hr$^{-1}$, said solid catalyst material containing a synthetic amorphous solid prepared by the steps of hydrolyzing and polymerizing in the presence of water a silane having the formula R(Si)X$_3$, wherein R is a nonhydrolyzable organic group, X is a hydrolyzable group and (Si) is selected from the group consisting of

and

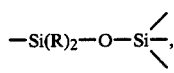

and calcining the polymerized product, said silane being admixed with a second compound, R$'_n$MY$_m$, wherein R$'$ is selected from the group consisting of the same groups as R, Y is selected from the group consisting of the same groups as X and oxygen, M is at least one member selected from the group consisting of the elements of Group VIII of the Periodic Table, m is any number greater than 0 and up to 8 and n is from 0 to any number less than 8.

2. The process of claim 1 wherein R of said catalyst material is a member selected from the group consisting of alkyl, cycloalkyl, aryl, alkenyl, cycloalkenyl and said members hydroxy-substituted, halogen-substituted and amino-substituted.

3. The process of claim 1 wherein X of said catalyst material is a member selected from the group consisting of halogen and alkoxy of from 1 to 10 carbon atoms, alkali metaloxy, alkaline earth metaloxy, carboxy and amino.

4. The process of claim 3 wherein X is chlorine.

5. The process of claim 3 wherein X is alkoxy.

6. The process of claim 5 wherein X is methoxy.

7. The process of claim 4 wherein R(Si)X$_3$ is selected from the group consisting of phenyl trichlorosilane, (C$_6$H$_5$)$_3$Si—O—SiCl$_3$, methyl trichlorosilane, ethyl trichlorosilane, dodecyl trichlorosilane and mixtures thereof.

8. The process of claim 1 wherein the calcination step in preparation of said catalyst material is carried out at a temperature of from about 200° C. to about 600° C.

9. The process of claim 1 wherein there is present in the final calcined catalyst material a member selected from the group consisting of platinum and palladium.

10. The process of claim 1 wherein there is present in the hydrolysis and polymerization steps in preparation of said catalyst material an inorganic compound consisting of an anion of M and Y and a cation selected from the group consisting of hydrogen, alkali metal, alkaline earth metal and ammonium.

11. The process of claim 10 wherein said inorganic compound is selected from the group consisting of sodium ethyl chloroplatinate and chloroplatinic acid.

12. The process of claim 1 wherein the steps of hydrolyzing and polymerizing in preparation of said catalyst material are carried out in the presence of water and an organic solvent.

13. The process of claim 12 wherein the organic solvent is an alcohol.

14. The process of claim 13 wherein the alcohol is methanol.

15. The process of claim 1 wherein the steps of hydrolyzing and polymerizing in preparation of said catalyst material are carried out in the presence of water and a base.

16. The process of claim 15 wherein the base is selected from the group consisting of pyridine and triethylamine.

17. The process of claim 1 wherein said oxygen is present in excess of that stoichiometrically required for complete combustion by at least about 50 percent.

* * * * *